US012781028B2

(12) United States Patent
Um et al.

(10) Patent No.: US 12,781,028 B2
(45) Date of Patent: Nov. 3, 2026

(54) POLYMER COMPOSITION AND PREPARATION METHOD THEREFOR

(71) Applicant: YOUREH CO., LTD., Hanam-si (KR)

(72) Inventors: Hyang Mae Um, Seoul (KR); Eui Jin Hwang, Suwon-si (KR)

(73) Assignee: YOUREH CO., LTD., Hanam-si (KR)

( * ) Notice: Subject to any disclaimer, the term of this patent is extended or adjusted under 35 U.S.C. 154(b) by 353 days.

(21) Appl. No.: 18/558,293

(22) PCT Filed: May 13, 2022

(86) PCT No.: PCT/KR2022/006946
§ 371 (c)(1),
(2) Date: Oct. 31, 2023

(87) PCT Pub. No.: WO2022/240264
PCT Pub. Date: Nov. 17, 2022

(65) Prior Publication Data

US 2024/0218164 A1 Jul. 4, 2024

(30) Foreign Application Priority Data

May 14, 2021 (KR) ........................ 10-2021-0063040

(51) Int. Cl.
*C08L 5/08* (2006.01)
*A61L 15/22* (2006.01)
(Continued)

(52) U.S. Cl.
CPC ............... *C08L 5/08* (2013.01); *A61L 15/225* (2013.01); *A61L 15/42* (2013.01); *A61L 15/46* (2013.01);
(Continued)

(58) Field of Classification Search
None
See application file for complete search history.

(56) References Cited

U.S. PATENT DOCUMENTS 9,220,761 B2 12/2015 Barnett et al.
2009/0202640 A1 8/2009 Paoletti et al.

FOREIGN PATENT DOCUMENTS

CA 2 739 499 A1 4/2010
JP 2014088353 A * 5/2014
(Continued)

OTHER PUBLICATIONS

Djafari et al., "Study and Preparation of Multifunctional Poly(L-Lysine)@Hyaluronic Acid Nanopolyplexes for the Effective Delivery of Tumor Suppressive MiR-34a into Triple-Negative Breast Cancer Cells", Materials 2020, 13, 5309, 9 pages.
(Continued)

*Primary Examiner* — Isis A Ghali
(74) *Attorney, Agent, or Firm* — Vorys, Sater, Seymour and Pease LLP; Mih Suhn Koh

(57) ABSTRACT

Provided are a method for preparing a composition having a form and use applicable in various fields from a mixed aqueous solution obtained by dissolving an anionic polymer and a cationic polymer in an aqueous solution without any precipitation/suspension phenomenon, comprising adding an electrolyte for a mixed aqueous solution comprising an anionic polymer and a cationic polymer in an amount that an ionic strength (I) of the electrolyte in the mixed aqueous solution satisfies a condition of: (1) (16.5×(number of moles of polymer used in smaller amount among the anionic polymer and the cationic polymer)×$(NIG)^2$)≤ionic strength (I)≤(30×number of moles of the anionic polymer); or (2) 0.001<ionic strength (I)<(16.5×(number of moles of polymer used in smaller amount among the anionic polymer and the cationic polymer)×$(NIG)^2$) and adjusting pH to 7.0 to 8.3.

4 Claims, 4 Drawing Sheets

(51) Int. Cl.
*A61L 15/42* (2006.01)
*A61L 15/46* (2006.01)
*A61L 15/64* (2006.01)
*C08L 5/04* (2006.01)

(52) U.S. Cl.
CPC ................. *A61L 15/64* (2013.01); *C08L 5/04* (2013.01); *A61L 2300/404* (2013.01); *C08L 2201/06* (2013.01); *C08L 2203/02* (2013.01); *C08L 2205/025* (2013.01)

(56) References Cited

FOREIGN PATENT DOCUMENTS

| | | | |
|---|---|---|---|
| JP | 6006084 | B2 | 10/2016 |
| KR | 1999-0049107 | A | 7/1999 |
| KR | 10-2018-0083367 | A | 7/2018 |
| WO | 2007/135116 | A1 | 11/2007 |

OTHER PUBLICATIONS

Khademhosseini et al., "Layer-by-layer deposition of hyaluronic acid and poly-L-lysine for patterned cell co-cultures", Biomaterials 25 (2004) 3583-3592.

* cited by examiner

POLYMER COMPOSITION AND PREPARATION METHOD THEREFOR

TECHNICAL FIELD

The present invention relates to a polymer composition comprising an anionic polymer, a cationic polymer and an electrolyte, and a method for preparing the same.

BACKGROUND ART

Biodegradable polymers have been developed into three types: "bioabsorbable medical materials," "biodegradable plastics," and "bio-based materials," depending on their use. The biodegradable polymer developed first is a medical material which is absorbable in living body, and its commercialization was initiated with a soluble surgical thread of poly-glycolic acid in the late 1970s. The importance of biodegradable polymers in this field has been growing for their applications into a regenerative medicine. Over the past two centuries, much development has been made for applying biodegradable polymer materials for biomedical purposes. Biodegradable polymer materials are excellent and representative materials for developing therapeutic tools. Representative examples include temporary artificial organs, 3D porous materials to form scaffolds for cell tissue engineering, controlled/sustained-release drug delivery means and the like. In order to be applied for those applications, it is required a material having specific physical, chemical, biological, biomedical and degradation properties. A variety of natural and synthetic polymers to be degraded through a hydrolysis or enzymatic action have been examined. Most of the currently commercialized biodegradable polymers are a natural polymer such as collagen, or a synthetic polymer such as poly(α-ester). Successful development of a biodegradable polymer implant depends on how to design and modify existing biomaterials for achieving appropriate biocompatibility, biodegradability and physical properties. There is a paradigm shift moving from biostable biomaterials to biodegradable biomaterials. In view of current trends, it seems that most permanent prosthetic materials used for temporary treatment would be replaced by biodegradable tools to repair and regenerate damaged cells. Natural polymers (e.g., collagen) to be degraded by enzymes have been used biomedically for thousands of years, but biodegradable synthetic polymers have been used since late 1960s. In particular, groundbreaking developments have been made in the past 20 years. What served as a driving force was the emergence of new biomedical technology. This is because biodegradability-based materials are needed in the fields such as tissue engineering, regenerative medicine, gene therapy, drug delivery control, biological nanotechnology and the like. Excellent biocompatibility is a prerequisite for applying the polymer materials to living organisms. Biodegradable materials have to be slowly degraded themselves, and ultimately be converted into substances harmless to living organisms. Otherwise, various foreign body reactions such as an inflammatory response, a fibrosis reaction and the like might occur in vivo. Therefore, it is very important that the material is degraded and discharged. Applications of biodegradable materials have been expanding into the medical and pharmaceutical fields, and they will gradually be expanded together with the progress of micro- and nano-technologies. Due to the diversity of polymer materials, the polymer materials have been replacing other materials such as metals, alloys and ceramics which have been previously used as biomaterials.

Meanwhile, the cosmetic product market has been rapidly growing every year, and such market growth is based on the rapid development of cosmetics technology. Existing approaches used for the purpose of beauty are expanding, and functional cosmetic product market, such as highly functional cosmetic product to which the concept of prevention and treatment of diseases is introduced, and functional cosmetic product exhibiting various functions such as whitening, anti-wrinkle, UV protection, anti-inflammatory, anti-obesity properties, etc. have also recently grown rapidly. With those changes and developments in the cosmetics industry, new-concept cosmetic products are continuously being released onto the market through the development of new materials and new technology, and technological convergence with other industries. It can be said that the development of domestic cosmetics technology began in the 1960s. At that time, most cosmetics technology was focused on the manufacture of cosmetic products. In particular, the main focus was on interfacial research related to emulsification. In the beginning, research was mainly conducted to improve the dispersion stability of products using emulsifying agents, to control a manufacturing process and to improve the feeling of use. In the 1980s, there was high interest in skin aging and whitening, and thus, much research was conducted to solve those problems. To develop efficacious materials with biological methods and to efficiently deliver the effective materials to the skin, products incorporating encapsulation technology such as liposomes have been released. In the 1990s, more efficacy-oriented products were released, and effects such as whitening and wrinkle prevention became important in addition to moisturizing and protective functions. To provide effects as such, various materials including vitamins, natural extracts, and the like have been developed, and much effort has been focused on developing formulation technologies that can stabilize those ingredients within the products and can be effectively absorbed the same into the skin. In the 21st century, research on technology in the cosmetics industry has been actively conducted in the field of dermatology to suppress aging, inhibit melanin production, and alleviate hair loss, acne, skin irritation and the like. In the field of materials, search for natural ingredients having those efficacies and synthesis of new substances and derivatives showing new effects have been actively conducted. In recent years, herbal plant extracts obtained from angelica root, ginseng and the like, and plant extracts obtained from chamomile, rose and the like have been widely used, and biomolecules such as ceramide, which is a lipid component between keratinocytes, have also been commercialized. In addition, drug delivery technology to be absorbed the developed efficacious ingredients into the skin, technology for stabilizing unstable efficacious substances, and formulation technology for solubilizing poorly soluble efficacious substances have been developed in combination with fluid and nanotechnology, and have been used in products.

As such, the biocompatible polymers are expected to be utilized in various fields with their advantages. However, when polymers with opposite charges are mixed, precipitation or turbidity occurs, which makes it impossible to prepare a solution with precise contents, and the characteristics of functional polymers that utilize positive and negative charges are lost or reduced. Therefore, there is a need to solve those problems.

U.S. Pat. No. 9,220,761, Materials 2020, 13, 5309, Biomaterials. 2004 August; 25(17): 3583-92, Canadian Patent Publication No. 2739499 and the like disclose a process of mixing poly-L-lysine with a counterion polymer. Such prior art related to the prevention of the formation of precipitate by adjusting pH as a reaction condition, and the pH adjustment is essential in setting reaction conditions. When the pH is adjusted, it is possible to avoid the formation of precipitate because the ionization tendency is adjusted according to the pKa value of the ionic polymer. However, when the charge characteristics of the ionic polymer are used, for example, poly-L-lysine exhibits antibiotic or bacteriostatic functions due to its positive charge characteristics, but when the ionization tendency is reduced or suppressed, those functions are lost, and thus, it does not meet the initial purpose of use of poly-L-lysine. Therefore, there is a need to develop technology for mixing ionic polymers with opposite charges in a homogeneous state while maintaining the functions to be obtained from the charge characteristics of the ionic polymers.

DETAILED DESCRIPTION OF INVENTION

Technical Problem

The present invention is to solve the above problems in the development of polymer composite materials, and thus, it is an object of the present invention to provide a method for preparing a polymer composition to prevent any precipitation or suspension phenomenon which may occur when mixing polymers with opposite charges, so as to prepare a solution with precise contents, by which makes it possible to maintain the characteristics of functional polymers with a positive or negative charge, and a polymer composition prepared by the method.

It is another object of the present invention to provide a polymer composition in the form of a liquid, or a dried product such as foam, a pad, a film, a stick, a sponge, thread, powder and the like, which makes it possible to be used for a wound dressing, a hemostatic material, suture thread, a cosmetic product, a feminine hygiene product or the like.

Technical Solution

Technical solutions to the above technical problems in the present invention are as follows:

1. A method for preparing a polymer composition comprising an anionic polymer and a cationic polymer, comprising:

(1) adding an electrolyte for a mixed aqueous solution comprising an anionic polymer and a cationic polymer in an amount that an ionic strength (I) of the electrolyte in the mixed aqueous solution satisfies a condition of (16.5×(number of moles of polymer used in smaller amount among the anionic polymer and the cationic polymer)×$(NIG)^2$)≤ionic strength (I)≤(30×number of moles of the anionic polymer); or (2) adding an electrolyte for a mixed aqueous solution comprising an anionic polymer and a cationic polymer in an amount that an ionic strength (I) of the electrolyte in the mixed aqueous solution satisfies a condition of 0.001<ionic strength (I)<(16.5×(number of moles of polymer used in smaller amount among the anionic polymer and the cationic polymer)×$(NIG)^2$) and adjusting pH to 7.0 to 8.3, wherein the number of moles of the polymer in (1) and (2) represents a value calculated by weight of the polymer/mass of repeating unit of the polymer, and NIG represents the higher number among the number of charge groups in the repeating units of the anionic polymer and the cationic polymer.

2. The method for preparing the polymer composition according to 1 above, comprising: preparing an aqueous anionic polymer solution, followed by adding an electrolyte to the aqueous anionic polymer solution to satisfy the condition of (1) or (2), and then adding a cationic polymer or an aqueous solution of the cationic polymer.

3. The method for preparing the polymer composition according to 1 above, wherein the anionic polymer and the cationic polymer are mixed at a molar ratio of 1.5:0.001 to 0.01:2.4 by number of moles of repeating unit of the polymers.

4. The method for preparing the polymer composition according to 1 above, wherein the anionic polymer is selected from the group consisting of hyaluronic acid, alginic acid, polyglutamic acid, carboxymethyl cellulose, sodium carboxymethyl dextran, sodium carboxymethyl beta-glucan and sodium carboxymethyl starch.

5. The method for preparing the polymer composition according to 1 above, wherein the cationic polymer is selected from the group consisting of polylysine, chitosan, protamine, polyarginine, poly(ethyleneimine) and poly(2-dimethyl(aminoethyl) methacrylate).

6. The method for preparing the polymer composition according to 1 above, wherein the electrolyte is selected from the group consisting of sodium chloride, potassium chloride, sodium citrate, sodium ascorbyl phosphate, sodium gluconate, sodium glucuronate, sodium malate, sodium borate, sodium acetate, sodium aspartate, sodium phosphate, calcium chloride, calcium carbonate, calcium hydroxide, calcium phosphate, calcium gluconate, calcium oxalate, calcium oxide, magnesium ascorbyl phosphate, magnesium aspartate, magnesium chloride, magnesium sulfate and magnesium stearate.

7. The method for preparing the polymer composition according to 1 above, wherein the anionic polymer or cationic polymer has a number average molecular weight of 1,000 Da to 3,000,000 Da.

8. A polymer composition prepared according to the method of any one of 1 to 7 above, comprising an anionic polymer, a cationic polymer and an electrolyte.

9. The polymer composition according to 8 above, wherein the anionic polymer and the cationic polymer are mixed at a molar ratio of 1.5:0.001 to 0.01:2.4 by number of moles of repeating unit of the polymers.

10. The polymer composition according to 8 above, provided in a liquid form, or a dried product in the form of foam, a pad, a film, a stick, a sponge, thread or powder.

11. The polymer composition according to 10 above, used for a wound dressing, a hemostatic material, suture thread, a cosmetic product or a feminine hygiene product.

Advantageous Effects

In accordance with the present invention, a mixed aqueous solution of an anionic polymer and a cationic polymer and a dried product of the mixed aqueous solution were provided, thereby making it possible to avoid any suspension phenomenon caused by precipitation or partial aggregation when preparing a dried product of a combination of ingredients by mixing polymers with opposite charges, so as to prepare a mixed aqueous solution satisfy the purpose, from which a liquid composition, or a dried product in various forms such as foam, pad, film, stick, sponge, thread, powder and the like can be provided.

The liquid composition or the dried product such as foam, pad, film, stick, sponge, thread, powder and the like provided in the present invention can be applied for a wound dressing, a hemostatic material, suture thread, a cosmetic product, a feminine hygiene product and the like.

BRIEF DESCRIPTION OF DRAWINGS

(FIG. 1A: Example 1, FIG. 1B: Example 5, FIG. 1C: Example 7, FIG. 1D: Example 13, FIG. 1E: Example 15, and FIG. 1F: Comparative Example 1).

(FIG. 2A: Example 1, and FIG. 2B: Comparative Example 1).

(FIG. 3A: Example 1, and FIG. 3B: Comparative Example 1).

DETAILED DESCRIPTION OF EMBODIMENTS

Figure 1A:
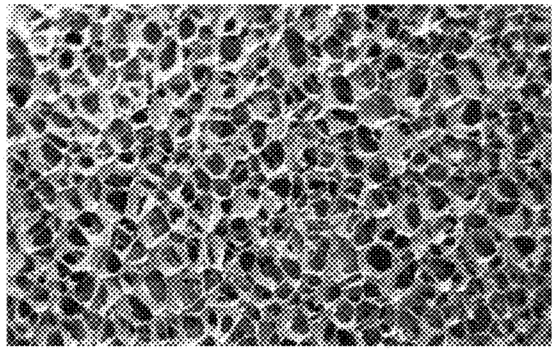
FIGS. 1A to 1E and FIG. 1F are high-resolution scanning microscope (transmission electron microscope; SEM) images of pads prepared in Examples 1, 5, 7, 13 and 15 of the present invention, and Comparative Example 1, respectively

The present invention relates to a method for preparing a polymer composition, wherein an anionic polymer and a cationic polymer are mixed and dissolved in an aqueous solution without any precipitation/suspension phenomenon to obtain a mixed aqueous solution in the form and use applicable in various fields, the method comprises:

(1) adding an electrolyte for a mixed aqueous solution comprising an anionic polymer and a cationic polymer in an amount that an ionic strength (I) of the electrolyte in the mixed aqueous solution satisfies a condition of (16.5×(number of moles of polymer used in smaller amount among the anionic polymer and the cationic polymer)×(NIG)$^2$)≤ionic strength (I)≤(30×number of moles of the anionic polymer); or (2) adding an electrolyte for a mixed aqueous solution comprising an anionic polymer and a cationic polymer in an amount that an ionic strength (I) of the electrolyte in the mixed aqueous solution satisfies a condition of 0.001<ionic strength (I)<(16.5×(number of moles of polymer used in smaller amount among the anionic polymer and the cationic polymer)×(NIG)$^2$) and adjusting pH to 7.0 to 8.3, wherein the number of moles of the polymer in (1) and (2) represents a value calculated by weight of the polymer/mass of repeating unit of the polymer, and NIG represents the higher number among the number of charge groups in the repeating units of the anionic polymer and the cationic polymer. Accordingly, when both of the numbers of charge groups in repeating units of the anionic polymer and the cationic polymer are 1, NIG is 1, and when the number of charge groups in repeating unit of one of the anionic and cationic polymers is 1 and the number of charge groups in repeating unit of the other of the anionic and cationic polymers is 2, or when both of the numbers of charge groups in repeating units of the anionic and cationic polymers are 2, NIG is 2.

Meanwhile, the ionic strength (I) of the electrolyte is a value calculated by the following Equation 1:

$$I = \frac{1}{2}\sum_{i=1}^{n} C_i Z_i^2 \qquad \text{Equation 1}$$

wherein n represents the number of ions of the electrolyte in a solution, i represents specific ions of the electrolyte, Ci represents the mole number of ions of the electrolyte in the solution, and Zi represents a valence of ions of the electrolyte.

In the present invention, under the condition of (1) above, the electrolyte is added in an amount that ionic strength of the electrolyte calculated by Equation 1 is equal to or greater than 16.5×(number of moles of polymer used in smaller amount among the anionic polymer and the cationic polymer)×(NIG)$^2$ and equal to or less than 30 times of the number of moles of the anionic polymer. In the present invention, the electrolyte is added in an amount that the ionic strength value of the electrolyte is equal to or greater than 16.5×(number of moles of polymer used in smaller amount among anionic and cationic polymers)×(NIG)$^2$, so as to prepare a mixed aqueous solution of ionic polymers with opposite charges without any precipitation or suspension phenomenon. When the electrolyte is added in an amount that the ionic strength value becomes less than lower limit as defined above, precipitation occurs even with slight changes in pH, temperature, concentration and the like when preparing the mixed aqueous solution, which makes it difficult to ensure stability of the mixed aqueous solution, and thus, it is undesirable. The anionic polymer serves to determine the viscosity of the mixed aqueous solution and gives tension during freeze-drying. Therefore, in order to maintain tension and to prevent the dried product of the mixed aqueous solution from breaking, it is preferable to limit the amount of electrolyte to be added such that the ionic strength value does not exceed 30 times of the number of moles of the anionic polymer.

In the present invention, under the condition of (2) above, the electrolyte is added in an amount that the ionic strength value of the electrolyte is greater than 0.001 and less than 16.5×(number of moles of polymer)×(NIG)$^2$, and pH of the mixed aqueous solution is adjusted to 7.0 to 8.3. This is because even when a smaller amount of the electrolyte is added compared to the condition of (1) above, the same effect as in the condition of (1) can be achieved by adjusting pH of the mixed aqueous solution to 7.0 to 8.3.

In the present invention, the anionic polymer may be selected from the group consisting of hyaluronic acid, alginic acid, polyglutamic acid, carboxymethyl cellulose, sodium carboxymethyl dextran, sodium carboxymethyl beta-glucan and sodium carboxymethyl starch, but not limited thereto, and any anionic polymer having at least one negative charge group in its repeating unit may be used.

In the present invention, the cationic polymer may be selected from the group consisting of polylysine, chitosan, protamine, polyarginine, poly(ethyleneimine) and poly(2-dimethyl(aminoethyl) methacrylate), but not limited thereto, and any cationic polymer having at least one positive charge group in its repeating unit may be used.

In one embodiment of the method for preparing a polymer composition according to the present invention, an aqueous anionic polymer solution is prepared at first, to which an electrolyte is added so as to satisfy the condition of (1) or (2) as defined above, and then a cationic polymer or an aqueous solution of the cationic polymer is added to obtain a mixed aqueous solution. Herein, the mixing ratio of the anionic polymer and the cationic polymer is in a range of 1.5:0.001 to 0.01:2.4, preferably 1.0:0.002 to 0.1:2.0, more preferably 0.5:0.01 to 0.01:1.0, and most preferably 0.1:0.003 to 0.01:0.01 by mole numbers of repeating unit in the polymers. In the present invention, the anionic polymer and the cationic polymer are mixed in this ratio so as to secure the viscosity of the mixed aqueous solution, and to secure tension, anti-inflammatory effect and moisturizing property from the anionic polymer and bacteriostatic activity from the cationic polymer in the dried product after freeze-drying.

In the present invention, the electrolyte may be an organic or inorganic salt selected from the group consisting of sodium chloride, potassium chloride, sodium citrate, sodium ascorbyl phosphate, sodium gluconate, sodium glucuronate, sodium malate, sodium borate, sodium acetate, sodium aspartate, sodium phosphate, calcium chloride, calcium carbonate, calcium hydroxide, calcium phosphate, calcium gluconate, calcium oxalate, calcium oxide, magnesium ascorbyl phosphate, magnesium aspartate, magnesium chloride, magnesium sulfate and magnesium stearate, but not limited thereto.

Hyaluronic acid (hereinafter, sometimes referred to as "HA") is a long linear polysaccharide consisting of β-D-glucuronic acid and β-D-N-acetylglucosamine connected to each other via beta bonds, and it is a biodegradable and biocompatible natural polymer widely present in nature having a wide molecular weight distribution from 1,000 Da to 10,000,000 Da.

Formula (1) below represents the structure of a repeating unit of hyaluronic acid, and the number of charge groups (anionic groups) in the repeating unit is 1.

Formula 1

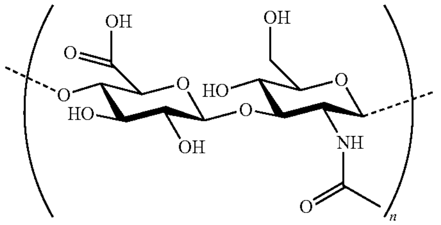

By binding with a large amount of water, hyaluronic acid is present in large quantities in the vitreous body of the eye, joint fluid, cartilage and skin in a highly viscous gel state, by which it has been known to function of lubricating joints, rendering flexibility to the skin and protecting the skin from bacteria with its high viscosity. Accordingly, hyaluronic acid has been used in many fields such as degenerative arthritis, cataracts, wrinkle improvement, drug delivery, stem cell support, moisturizing cosmetic product and the like. In addition, it has been reported that hyaluronic acid is present in large amounts in extracellular matrix of tissue, by which it regulate cell differentiation and proliferation, and its wound healing effect (Erika Nyman et al., J. Plasr Surg Hand Surg. 2013; 47; 89-92) and wound healing mechanism (Richard D Price et al., Am J Clin Dermatol; 2005; 6(6) 393-402) have also been reported.

Recent studies have also reported that low-molecular-weight hyaluronic acid has a pharmacological activity which induces regeneration of blood vessels around damaged tissue, thereby efficiently healing wounds. Based on such features, hyaluronic acid has been widely used in the fields of wound healing, arthritis therapy, drug delivery systems and tissue engineering. In addition, it is also used as an anti-adhesion agent due to its excellent biocompatibility, biodegradability and tissue adhesion-preventing properties. However, conventional hyaluronic acid provided in a sodium salt has been known to have no hemostatic effect.

Poly-gamma-glutamic acid (γ-PGA) is a safe and edible biomaterial naturally produced from *Bacillus subtilis*. γ-PGA is an anionic polypeptide having a structure in which D- or L-glutamate is polymerized via γ-amide linkages. To date, in view of chemical structure, it has found three types of γ-PGA including a homo-polymer composed of D-glutamate, a homo-polymer composed of L-glutamate, and a copolymer in which D-glutamate and L-glutamate are randomly arranged. Among them, a representative has a copolymer structure which is isolated from *Bacillus subtilis*-based Natto and Cheonggukjang. γ-PGA having a molecular weight of 10 to 10,000 kDa was produced using *Bacillus subtilis* isolated from Natto. In recent years, γ-PGA having a high molecular weight of 1,000 kDa or more have been produced using *Bacillus subtilis* extracted from Cheonggukjang, a traditional Korean food. γPGA has been used in various fields of food, industry, environment and medicine as a health food for preventing osteoporosis, a food stabilizer, a chelating agent for wastewater disposal, a new biomaterial, a moisturizer, a cosmetic product, a liquid crystal display (LCD) material, a drug deliverer, a gene vector and the like.

Alginic acid is a natural polymer that is extracted from brown algae such as seaweed and kelp, and used in various biomedical applications. Alginic acid has advantages of excellent biocompatibility, low toxicity and being inexpensive. In addition, alginic acid binds with a divalent cation (e.g., $Ca^{2+}$) to relatively easily form a hydrogel. In particular, alginic acid has a molecular structure of a block copolymer composed of D-mannuronic acid and L-guluronic acid, and L-guluronic acid block binds with a divalent cation to form a hydrogel, and thus, length of L-guluronic acid block is an important factor in determining physical properties of the alginate hydrogel.

Formula 2 below shows the structure of repeating unit of alginic acid, and the number of charge groups (anionic groups) in its repeating unit is 2.

Formula 2

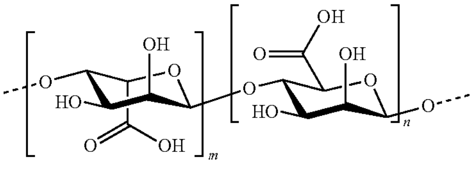

Alginic acid has been used as a medical material in various fields as well as tissue engineering, and has been known to have excellent biocompatibility and low toxicity in vitro and in vivo conditions. It has been reported that commercially available alginic acid has low toxicity and causes almost no immune response in animal experimentation. It has been known that alginic acid is not degraded under physiological conditions, and alginate gel can be disintegrated and dissolved with release of divalent cations, which act as a cross-linking agent in the alginate hydrogel, through an exchange reaction with monovalent cations (e.g., $Na^+$) present in the living body. However, because commercially available alginic acid has a large molecular weight, it is difficult to pass through kidney and be excreted out of the body after being dissolved. A representative method of imparting degradability to alginic acid is a partial oxidation. When alginic acid is partially oxidized to introduce aldehyde groups into its main chain, it can be degraded in a physiological saline. The biodegradation rate of partially oxidized alginic acid can be controlled based on degree of oxidation, pH and temperature.

Polylysine (ε-poly-L-lysine; hereinafter, sometimes referred to as "PLL") is a combination of 25 to 35 L-lysines, which is a strongly basic amino acid and has a positive (+) charge.

Formula 3 below shows structure of repeating unit of polylysine, and the number of charge groups (cationic groups capable of forming a salt with a carboxylic acid via an ionic bond) in the repeating unit is 1.

Formula 3

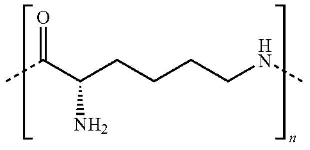

Polylysine having a positive charge as such ionically binds with negatively charged cell membrane of microorganisms, by which it exhibits bactericidal activity inhibiting the growth of microorganisms. Due to such features, PLL has been widely used as a natural antibacterial agent (a natural preservative) or a food preservative (a natural preservative). Polylysine shows antibacterial activity against all bacteria (Gram-positive and -negative bacteria, and fungi) because it has a wide antibacterial spectrum and its antibacterial activity is maintained with no big change in minimum inhibitory concentration (MIC) in a weak acidic to neutral range (pH 4.0 to 8.0) due to its stability even under pH changes. In addition, polylysine has no decrease in antibacterial activity by heat because it is stable against heat. Moreover, it has been known that polylysine induces aggregation of platelets and that its ability to induce aggregation of platelets depends on its molecular size.

Chitin is a linear polysaccharide, in which N-acetyl-D-glucosamines (GlcNAcs) are linked via a β-1,4 bond, and is a mucopolysaccharide having chemical and crystalline structure similar to cellulose. Even though chitin is a low-toxic substance having in vivo digestibility, biocompatibility, a stimulatory effect on epidermal cell growth-stimulating factors and the like, it has been rarely used and maintained its position only as a chitosan intermediate. It is because chitin is insoluble in typical solvents, which makes it difficult to perform molding processing. Chitosan is a de-acetylated chitin, which is insoluble in water or a base, but soluble in a weak acid such as lactic acid, citric acid, acetic acid and the like, and has properties of being degraded by the action of an enzyme, thereby being easily absorbed. The most ideal form is 100% de-acetylated one, which shows a crucial difference in efficacy. In general, when 60% or more de-acetylated, it is referred to as chitosan.

Formula 4 below shows structure of a repeating unit of chitosan, and the number of charge groups (cationic groups capable of forming a salt with a carboxylic acid via an ionic bond) in the repeating unit (a dimer) of chitosan is 2.

Formula 4

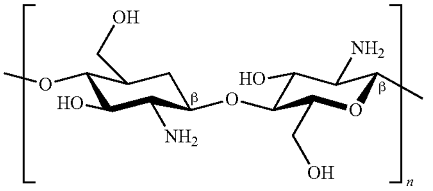

Meanwhile, in the case of polymers, such as alginic acid, which have a high relative charge density of the anionic group (carboxylic acid group) in the repeating unit, it is necessary to consider ionic strength similar to valence. In this case, the number of anionic groups (charge groups) in the repeating unit (a dimer) of alginic acid is 2, and the number of anionic groups (charge groups) in the repeating unit (a dimer) of hyaluronic acid is 1.

Therefore, when considering the concept of an ionic strength, if molarities of polymers in a solution are the same as 0.01 M, ionic strength of carboxylic acid group in repeating unit of hyaluronic acid would be $0.01\ M\times(-1)^2$, and ionic strength of carboxylic acid group in repeating unit of alginic acid would be $0.01\ M\times(-2)^2$. Therefore, the amount of an electrolyte required for alginic acid would be approximately 4 times of that required for HA. That is, for example, if the ratio of the ionic strength of sodium citrate to the concentration of PLL is 17:1 for hyaluronic acid, sodium citrate is required in a concentration corresponding to an ionic strength of approximately 68 times, that is, 4 times of 17 for a mixed solution of alginic acid and PLL. The same applies to other anionic or cationic polymers.

In addition, when adding a salt containing a monovalent ion such as sodium chloride, sodium citrate and the like, and a salt containing a divalent ion such as magnesium ascorbyl phosphate, magnesium aspartate, magnesium chloride and the like, even if ionic strength of an electrolyte in a solution is less than 16.5 times, for example, 15 to 1 times of the molarity of a cationic polymer, the same results can be obtained by mixing aqueous solutions of an anionic polymer and a cationic polymer at the above-described mixing ratio after adjusting pH of the solutions to 7.0 to 8.3. Considering pKa of the cationic polymer, such acidity adjustment allows the mixed aqueous solution to contain charges sufficient to exhibit activities, by which makes it possible to prepare an aqueous solution to meet the purpose of mixing.

In the present invention, the amount of an electrolyte to be added is determined based on ionic strength of the electrolyte so as to suppress aggregation from interaction between opposite charges of the polymers in the mixed aqueous solution, by which makes it possible to obtain a uniform mixed aqueous solution without any precipitation or suspension phenomenon regardless of the type of electrolyte to be used, when the polymers are mixed to satisfy the condition of (1) or (2) as defined above.

In the present invention, an anionic or cationic polymer having a number average molecular weight of 1,000 Da to 3,000,000 Da, preferably 3,000 Da to 2,000,000 Da, and more preferably 4,000 Da to 1,000,000 Da is used.

The present invention provides dried products having various shapes for use in various fields with a mixed aqueous solution of various polymers as described above.

Accordingly, the present invention also relates to a polymer composition prepared by the method as described above, which comprises an anionic polymer, a cationic polymer and an electrolyte.

According to one exemplary embodiment of the present invention, the polymer composition prepared by the above-described method may be used as it is in a liquid form, or may be dried with any method well known in the art, such as freeze-drying, drying under reduced pressure, spray drying and the like to, so that can be provided in the form of a porous dry foam, pad, film, stick, sponge, thread, powder, tablet and the like, which can be used as a wound dressing, a hemostatic material, suture thread, a cosmetic product, a feminine hygiene product and the like.

EXAMPLES

Hereinafter, the present invention will be described in more detail with reference to examples thereof. However, it should be understood that the examples presented below are only illustrative for carrying out the present invention, and are not intended to limit the scope of the present invention.

Examples 1 to 6: Preparation of Dried Products of Hyaluronic Acid and Polylysine Combination 4 g to 40 g of hyaluronic acid (molecular weight: 1,000 KDa) was added as an anionic polymer to 1,000 mL of purified water, and stirred for 12 hours. Sodium citrate or magnesium chloride as an electrolyte was mixed therewith at various ionic strengths, to which an aqueous solution of polylysine (molecular weight: 4,500 Da) as a cationic polymer was added and dissolved to obtain a mixed aqueous solution without any precipitation or suspension phenomenon.

The mixed aqueous solution in which any precipitation or suspension phenomenon did not occur was dispensed into a mold according to the shape of dried products, and then dried by a freeze-drying, drying under reduced pressure or a spray drying to prepare dried products in the form of a porous dried pad, film, stick and tablet.

Figure 1B:
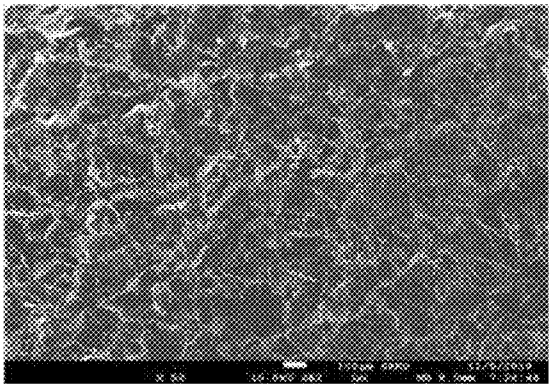

FIGS. 1A and 1B are high-resolution scanning microscope (transmission electron microscope; SEM) images of pads prepared in Examples 1 and 5 of the present invention (FIG. 1A: Example 1, and FIG. 1B: Example 5).

In addition, FIGS. 4 to 7 are images of the external appearances of dried products in the forms of pad, film, stick and tablet, respectively, prepared in Example 1 of the present invention.

The content (molarity) of HA, the amount and ionic strength of the electrolyte, the content (molarity) of PLL, and the ratio of the ionic strength of the electrolyte to the molarity of the polymer in the mixed aqueous solution are shown in Table 1 below.

TABLE 1

| Examples | HA content (molarity) | Amount (ionic strength) of electrolyte | PLL content (molarity) | Ionic strength of electrolyte:molarity of PLL |
|---|---|---|---|---|
| Example 1 | 4 g (0.01M) | 2.13 g (0.0495) sodium citrate | 0.5 g (0.003M) | 16.5:1 |
| Example 2 | 4 g (0.01M) | 2.49 g (0.0579) sodium citrate | 0.5 g (0.003M) | 19.3:1 |
| Example 3 | 4 g (0.01M) | 5.418 g (0.127) sodium citrate | 1.12 g (0.0077M) | 16.5:1 |
| Example 4 | 40 g (0.1M) | 4.99 g (0.116) sodium citrate | 1.00 g (0.0068M) | 17.0:1 |
| Example 5 | 4 g (0.01M) | 1.56 g (0.0495) magnesium chloride | 0.5 g (0.003M) | 16.5:1 |
| Example 6 | 4 g (0.01M) | 2.19 g (0.069) magnesium chloride | 0.61 g (0.0042M) | 16.5:1 |

Examples 7 to 12: Preparation of Dried Products of Alginic Acid and Polylysine Combination 3.98 g of alginic acid (molecular weight: 800 KDa) was added as an anionic polymer to 1,000 mL of purified water, and stirred for 12 hours. Sodium citrate or magnesium ascorbyl phosphate (MAP) was mixed therewith as shown in Table 2, to which an aqueous solution of polylysine (molecular weight: 4,500 Da) as a cationic polymer was added and dissolved to obtain a mixed aqueous solution without any precipitation or suspension phenomenon.

Figure 1C:
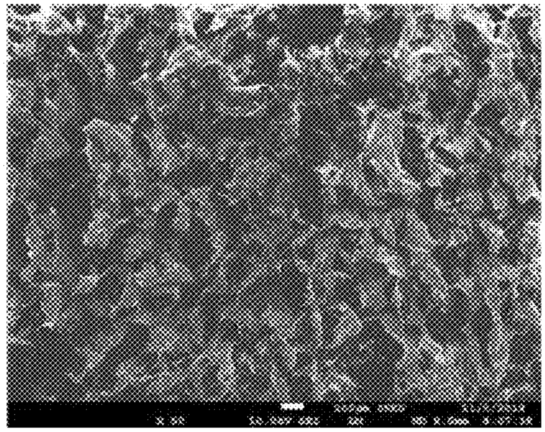

The aqueous solution in which any precipitation or suspension phenomenon did not occur was dispensed into a mold according to the shape of dried products, and freeze-dried to prepare dried products in the form of a porous dried pad or film. FIG. 1C is a high-resolution scanning microscope (transmission electron microscope; SEM) image of the dried pad prepared in Example 7 of the present invention.

The content (molarity) of alginic acid, the amount and ionic strength of the electrolyte, the content (molarity) of PLL, and the ratio of the ionic strength of the electrolyte to the molarity of the polymer in the mixed aqueous solution are shown in Table 2 below.

TABLE 2

| Examples | Alginic acid content (molarity) | Amount (ionic strength) of electrolyte | PLL content (molarity) | Ionic strength of electrolyte:molarity of PLL |
|---|---|---|---|---|
| Example 7 | 3.98 g (0.01M) | 8.5 g (0.198) sodium citrate | 0.5 g (0.003M) | 66:1 |
| Example 8 | 3.98 g (0.01M) | 9.16 g (0.213) sodium citrate | 0.5 g (0.003M) | 71:1 |
| Example 9 | 3.98 g (0.01M) | 21.93 g (0.508) sodium citrate | 1.12 g (0.0077M) | 66:1 |
| Example 10 | 39.8 g (0.1M) | 20.38 g (0.476) sodium citrate | 1.00 g (0.0068M) | 70:1 |

TABLE 2-continued

| Examples | Alginic acid content (molarity) | Amount (ionic strength) of electrolyte | PLL content (molarity) | Ionic strength of electrolyte:molarity of PLL |
|---|---|---|---|---|
| Example 11 | 3.98 g (0.01M) | 13.76 g (0.198) MAP | 0.5 g (0.003M) | 66:1 |
| Example 12 | 3.98 g (0.01M) | 20.15 g (0.290) MAP | 0.61 g (0.0042M) | 69:1 |

Examples 13 and 14: Preparation of Dried Products of Hyaluronic Acid and Chitosan Combination 4 g of hyaluronic acid (molecular weight: 1,000 KDa) as an anionic polymer was added to 1,000 mL of purified water, and stirred for 12 hours. Sodium citrate or magnesium ascorbyl phosphate (MAP) was mixed therewith at various ionic strengths, to which chitosan (molecular weight: 300 KDa) as a cationic polymer was dissolved as shown in Table 3, and then, pH was adjusted to 4.0 or below, and occurrence of precipitation was checked. Because the solubility of chitosan depends on pH, chitosan was dissolved in water, of which pH was adjusted to 3.0, and then a solution of the anionic polymer and the electrolyte was mixed after adjusting its pH to the same level as described above.

Figure 1D:
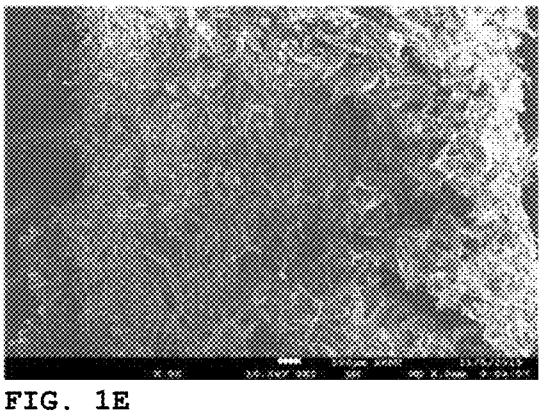

The aqueous solution in which any precipitation or suspension phenomenon did not occur was dispensed into a mold according to the shape of dried product, and freeze-dried or dried under reduced pressure in the same manner as in Examples 1 to 6 to prepare dried products in the forms of pad, film, stick and tablet. FIG. 1D is a high-resolution scanning microscope (transmission electron microscope; SEM) image of the dried pad prepared in Example 13 of the present invention.

The content (molarity) of HA, the amount and ionic strength of the electrolyte, the content (molarity) of chitosan, and the ratio of ionic strength of the electrolyte to the molarity of the polymer in the mixed aqueous solution are shown in Table 3 below.

TABLE 3

| Examples | HA content (molarity) | Amount (ionic strength) of electrolyte | Chitosan content (molarity) | Ionic strength of electrolyte:molarity of chitosan |
|---|---|---|---|---|
| Example 13 | 4 g (0.01M) | 8.8 g (0.205) sodium citrate | 1.2 g (0.003M) | 68.3:1 |
| Example 14 | 4 g (0.01M) | 14.11 g (0.203) MAP | 1.2 g (0.003M) | 67.7:1 |

Figure 1E:
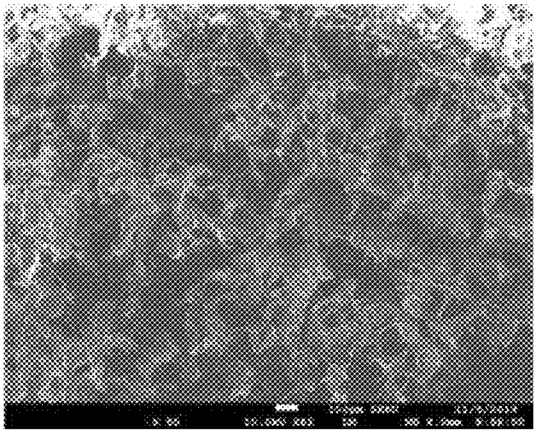

Examples 15 and 16: Preparation of Dried Products of Hyaluronic Acid and Polylysine Combination 4 g of hyaluronic acid (molecular weight: 1,000 KDa) as an anionic polymer was added to 1,000 mL of purified water, and stirred for 12 hours. As shown in Table 4, sodium citrate or magnesium ascorbyl phosphate (MAP) was mixed, and pH of resulting solutions was adjusted to 8.0 and 8.3, respectively. Thereafter, 0.5 g of polylysine (molecular weight: 4,500 Da) as a cationic polymer was dissolved, and occurrence of precipitation was then checked. The aqueous solution in which any precipitation or suspension phenomenon did not occur was dispensed into a mold according to the shape of dried product, and then freeze-dried or dried under reduced pressure in the same manner as in Examples 1 to 6 to prepare dried products in the forms of pad, film, stick and tablet. FIG. 1E is a high-resolution scanning microscope (transmission electron microscope; SEM) image of the dried pad prepared in Example 15 of the present invention.

The content (molarity) of HA, the amount and ionic strength of electrolyte, pH of the aqueous solution, the content (molarity) of PLL, and the ratio of the ionic strength of the electrolyte to the molarity of the polymer in the mixed aqueous solution are shown in Table 4 below.

TABLE 4

| Examples | HA content (molarity) | Amount (ionic strength) of electrolyte | PLL content (molarity) | Ionic strength of electrolyte:molarity of PLL |
|---|---|---|---|---|
| Example 15 | 4 g (0.01M) | 1.98 g (0.046) sodium citrate, pH = 8.3 | 0.7g (0.0047M) | 9.7:1 |
| Example 16 | 4 g (0.01M) | 1.06 g (0.045) magnesium chloride, pH = 8.0 | 1.0 (0.0068M) | 6.6:1 |

Comparative Examples 1 and 2: Preparation of Mixed Aqueous Solution of Hyaluronic Acid and Polylysine with Precipitation 4 g of hyaluronic acid (molecular weight: 1,000 KDa) as an anionic polymer was added to 1,000 mL of purified water, and stirred for 12 hours. As shown in Table 5, after sodium citrate or magnesium chloride was respectively mixed, into which 0.5 g of polylysine as a cationic polymer was dissolved, and then occurrence of precipitation was checked. Precipitation occurred, and precipitation reaction was continued even when polylysine (molecular weight: 4,500 Da) was further added until the concentration of polylysine became identical to that of hyaluronic acid. Resulting precipitate was introduced into a pad-shaped mold and then freeze-dried.

Figure 1F:
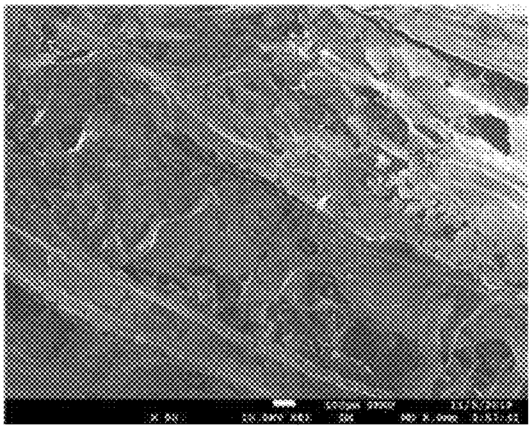

FIG. 1F is a high-resolution scanning microscope (transmission electron microscope; SEM) image of the freeze-dried pad prepared in Comparative Example 1. As shown in FIGS. 1A to 1E, the freeze-dried pads prepared from the mixed aqueous solution in which any precipitation phenomenon did not occur during mixing in Examples of the present invention have porous matrix structures, whereas FIG. 1F shows that the freeze-dried pad prepared from the mixed aqueous solution in which the precipitation phenomenon occurred during mixing do not have a porous structure.

Figure 2A:
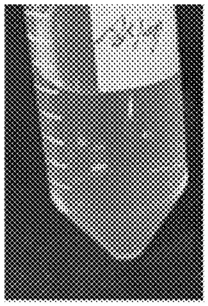
FIGS. 2A and 2B are images of mixed aqueous solutions of hyaluronic acid and polylysine prepared in Example 1 of the present invention and Comparative Example 1, respectively
Figure 2B:
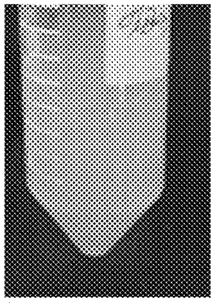

FIG. 2B is an image of the mixed aqueous solution of hyaluronic acid and polylysine prepared in Comparative Example 1. As shown in FIG. 2A, the mixed aqueous solution prepared in Example 1 was neither precipitated nor become turbid, whereas, as shown in FIG. 2B, the mixed aqueous solution prepared in Comparative Example 1 was turbid and precipitation phenomenon occurred.

TABLE 5

| Classification | HA content (molarity) | Amount (ionic strength) of electrolyte | PLL content (molarity) | Ionic strength of electrolyte:molarity of PLL |
|---|---|---|---|---|
| Comparative Example 1 | 4 g (0.01M) | 1.98 g (0.046) sodium citrate | 0.7 g (0.0047M) | 9.7:1 |
| Comparative Example 2 | 4 g (0.01M) | 1.06 g (0.045) magnesium chloride | 1.0 g (0.0068M) | 6.6:1 |

Experimental Example 1: Antibacterial Activity Test ASTM E 2315-16

The weights of the freeze-dried pads prepared in Examples 1 and 2, and Comparative Examples 1 and 2 were measured, to which bacterial culture media ten times of the weight of the dried pad were added and used for tests. The temperature for culture was 37° C., and a tryptic soy medium was used as a culture medium. Test strains were ATCC 6538 *Staphylococcus aureus*, ATCC 4352 *Klebsiella* peumoniae, ATCC 8739 *Escherichia coli* and ATCC 10145 *Pseudomonas aeruginosa.*

Figure 3A:
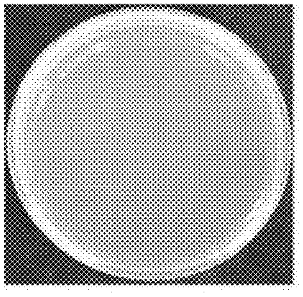
FIGS. 3A and 3B show results of comparing anti-microbial effects of pads prepared in Example 1 of the present invention and Comparative Example 1
Figure 3B:
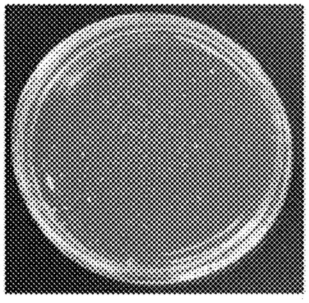
Figure 4:
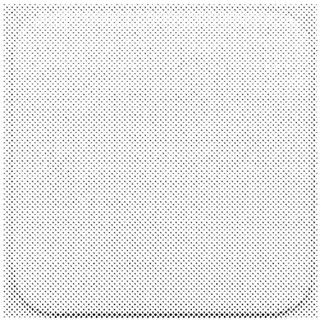
FIG. 4 is an image of the external appearance of a pad-type dried product prepared in Example 1 of the present invention.
Figure 5:
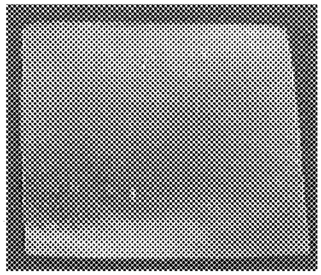
FIG. 5 is an image of the external appearance of a film-type dried product prepared in Example 1 of the present invention.
Figure 6:
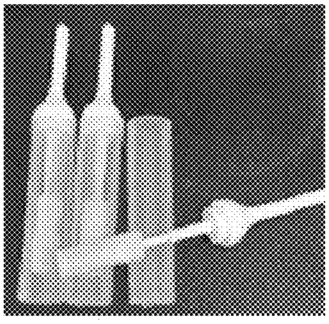
FIG. 6 is an image of the external appearance of a stick-type dried product prepared in Example 1 of the present invention.
Figure 7:
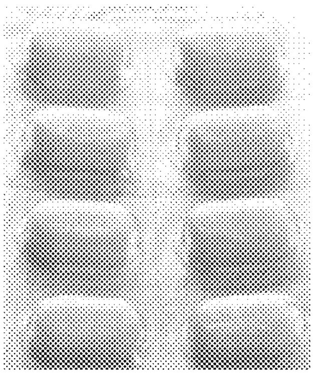
FIG. 7 is a blister-packaged image of a tablet-type dried product prepared in Example 1 of the present invention.

FIGS. 3A and 3B are images comparing the antimicrobial effects of the freeze-dried pads prepared in Example 1 of the present invention and Comparative Example 1 against *Staphylococcus aureus* (FIG. 3A: Example 1, and FIG. 3B: Comparative Example 1). FIG. 3A shows that the antibacterial activity against *Staphylococcus aureus* was maintained in the freeze-dried pad prepared in Example 1 because PLL having bacteriostatic and antibacterial activities was not precipitated in the mixed aqueous solution, by which no microbial growth was observed. However, FIG. 3B shows that the antibacterial activity against *Staphylococcus aureus* was lowered in the freeze-dried pad prepared in Comparative Example 1 because PLL was precipitated in the mixed aqueous solution, and thus microbial growth was observed.

Table 6 below shows the antibacterial activity test results for the freeze-dried pads prepared in Examples 1 and 2 of the present invention, and Comparative Examples 1 and 2. As shown in Table 6, it was found that the freeze-dried pads prepared in Examples 1 and 2 showed antibacterial activities, but the freeze-dried pads prepared in Comparative Examples 1 and 2 showed weak or no antibacterial activity.

TABLE 6

| Antibacterial effect: Bacterial count or Bacterial reduction rate (%) | | | | |
|---|---|---|---|---|
| Classification | ATCC 6538 *Staphylococcus aureus* | ATCC 4352 *Klebsiella peumoniae* | ATCC 8739 *Escherichia coli* | ATCC 10145 *Pseudomonas aeruginosa* |
| Example 1 | ND* | ND* | ND* | ND* |
| Example 2 | ND* | ND* | ND* | ND* |
| Comparative Example 1 | 15.4%** | 25.0%** | 18.8%** | 15.7%** |
| Comparative Example 2 | *** | *** | *** | *** |

*Not detected,
**Bacterial reduction rate = 100 × (1 − $10^{-\log 10\ reduction}$), $\log_{10}$ reduction = $\log_{10}$ (Initial bacterial count) − $\log_{10}$ (bacterial count after 24 hours),
*** When bacteria increased Experimental Example 2: Anti-Adhesion Test A rat cecum/abdominal wall abrasion model was used to evaluate anti-adhesion performances of the pad-type dried products prepared in Examples. As laboratory animals, five 7-week-old male Sprague-Dawley rats per group were used. In order to induce adhesion, experimental animals were anesthetized by intraperitoneal injection of Ketamin·○HCL (0.1 mL/100 g), of which abdomen was then shaved, disinfected with 70% ethanol and then incised to a size of approximately 4 to 5 cm along the midline of the abdomen. After cecum was taken out, 1.2 cm×1.2 cm area of its serous membrane was damaged with sterilized gauze to the extent of bleeding, and damage of the same size was inflicted on the facing abdominal cavity membrane. Two regions 1 cm away from frictionally damaged regions were fixed with 5-0 nylon suture thread such that damaged sides were faced with each other, so as to promote adhesion.

For a negative control, physiological saline was applied to the damaged region. For experimental groups, each of the pad-type dried products respectively prepared in Examples 1, 2, 7 and 13 was cut into 1 cm×1 cm size and attached to the damaged region, and then peritoneal membrane and skin were sutured. After surgery, the animals were raised for 1 week with plenty of water and food, and then sacrificed. The scores were added up with an adhesion evaluation system to obtain an average value. The results are shown in Table 7 below. All results were expressed in mean±standard error for each experimental group, and the significance for each group was tested at a level of $p<0.05$.

Degree of adhesion was evaluated from 0 to 5 according to the criteria as follows: 0: no adhesion, 1: one thin film-type adhesion, 2: two or more thin film-type adhesions, 3: concentrated punctate and thick adhesions, 4: concentrated lamellar adhesions, and 5: very thick vascularized adhesions, or one or more thick lamellar adhesions.

Adhesion strength was evaluated from 1 to 4 according to the criteria as follows: 1: film-type adhesion that can be separated with a very weak force, 2: adhesion which requires a moderate force to separate, 3: adhesion which requires significant pressure to separate, and 4: adhesion which is very strong so that it is difficult to remove, or that requires very high pressure to separate.

TABLE 7

| | Degree of adhesion | Adhesion strength | Adhesion area ($cm^2$) | Reduction of adhesion area (%) |
|---|---|---|---|---|
| Negative control | 3.8 ± 0.33* | 3.12 ± 0.10 | 0.80 ± 0.07 | 0 |
| Example 1 | 0.88 ± 0.08** | 0.92 ± 0.24 | 0.13 ± 0.08 | 83.75 |
| Example 2 | 0.34 ± 0.16 | 0.27 ± 0.44 | 0.03 ± 0.06 | 96.25 |
| Example 7 | 1.77 ± 0.69 | 1.45 ± 0.52 | 0.24 ± 0.10 | 70.0 |
| Example 13 | 0.78 ± 1.02 | 0.82 ± 0.65 | 0.06 ± 0.07 | 92.5 |

As shown in Table 7 above, tissue adhesion areas were significantly reduced in the groups to which the pad-type dried products prepared in Examples 1, 2, 7 and 13 were applied, compared to the negative control.

Experimental Example 3: Infection-Prevention Test in Infected Wound Model

After male Sprague-Dawley rats (n=10) weighing 280 g were anesthetized with isoflurane, an incision about 1 cm long was made at an interval of 2 cm or more on each side of their backs. An *E. coli* solution (0.2 mL, $1\times10^8$ CFU/mL) was injected subcutaneously into the incised site. For a polylysine group (PLL), the pad prepared in Example 2 was inserted, and the wound was then sutured. For a negative control, the wound was sutured with a hyaluronic acid pad (prepared by the applicant only with hyaluronic acid). The animals were transferred to individual cages with free access to food and water, and changes in body weight, body temperature and behavior of the animals were observed daily. The animals were sacrificed 4 days after transplantation, and tissue samples were excised from two sites and subjected to microbiological examination.

TABLE 8

| PLL group (test group) | HA (negative control) |
|---|---|
| 3.2* CFU | 136 CFU |

*$p \leq 0.01$,
CFU: Colony-forming unit

As shown in Table 8, it was found that the pads prepared in Examples of the present invention were effective in preventing infection also in an artificial infection model.

As described above, those skilled in the art to which the present invention pertains will understand that the present invention may be embodied in various modified forms. Therefore, it should be understood that the above-described embodiments are illustrative in all aspects. The scope of the present invention is defined by the claims described below rather than the detailed description, and all changes or modifications derived from the meaning and scope of the claims and equivalent concepts thereof should be construed as being included in the scope of the present invention.

The invention claimed is:

1. A method for preparing a polymer composition comprising an anionic polymer, a cationic polymer and an electrolyte, comprising:

(a) preparing an aqueous solution of the anionic polymer;

(b) adding the electrolyte to the aqueous solution obtained in step (a) in an amount such that, upon subsequent mixing with the cationic polymer, an ionic strength (I) attributable to the electrolyte in the mixed aqueous solution satisfies either condition (1) or (2) below; and (c) adding the cationic polymer, or an aqueous solution thereof, to the solution obtained in step (b):

(1) adding the electrolyte in an amount such that (16.5×(a number of moles of the polymer used in a smaller amount between the anionic polymer and the cationic polymer)×$(NIG)^2$)≤ionic strength (I)≤(19.3×a number of moles of the polymer used in a smaller amount between the anionic polymer and the cationic polymer×$(NIG)^2$), without adjusting a pH of the aqueous solution obtained in step (b); or (2) adding the electrolyte in an amount such that 0.001<ionic strength (I)<(16.5×(a number of moles of the polymer used in a smaller amount between the anionic polymer and the cationic polymer)×$(NIG)^2$), with adjusting the pH of the aqueous solution obtained in step (b) to 8.0 to 8.3, wherein the number of moles of the polymer in (1) and (2) represents a value calculated by dividing the weight of the polymer by the mass of the repeating unit of the polymer, and NIG represents the higher number among the numbers of charge groups in the repeating units of the anionic polymer and the cationic polymer, and wherein the anionic polymer is selected from hyaluronic acid and alginic acid, and the cationic polymer is selected from polylysine and chitosan.

2. The method according to claim 1, wherein the anionic polymer and the cationic polymer are mixed at a molar ratio of 1.5:0.001 to 0.01:2.4 by number of moles of repeating unit of the polymers.

3. The method according to claim 1, wherein the electrolyte is selected from the group consisting of sodium chloride, potassium chloride, sodium citrate, sodium ascorbyl phosphate, sodium gluconate, sodium glucuronate, sodium malate, sodium borate, sodium acetate, sodium aspartate, sodium phosphate, calcium chloride, calcium carbonate, calcium hydroxide, calcium phosphate, calcium gluconate, calcium oxalate, calcium oxide, magnesium ascorbyl phosphate, magnesium aspartate, magnesium chloride, magnesium sulfate and magnesium stearate.

4. The method according to claim 1, wherein the anionic polymer or cationic polymer has a number average molecular weight of 1,000 Da to 3,000,000 Da.

* * * * *